(12) United States Patent
Fujimaki et al.

(10) Patent No.: US 8,290,314 B2
(45) Date of Patent: Oct. 16, 2012

(54) OPTICAL WAVEGUIDE MODE SENSOR HAVING PORES

(75) Inventors: Makoto Fujimaki, Tsukuba (JP); Koichi Awazu, Tsukuba (JP)

(73) Assignee: National Institute of Advanced Industrial Science and Technology (JP)

( * ) Notice: Subject to any disclaimer, the term of this patent is extended or adjusted under 35 U.S.C. 154(b) by 428 days.

(21) Appl. No.: 12/438,050

(22) PCT Filed: Jun. 5, 2007

(86) PCT No.: PCT/JP2007/061366
§ 371 (c)(1),
(2), (4) Date: Feb. 19, 2009

(87) PCT Pub. No.: WO2008/023490
PCT Pub. Date: Feb. 28, 2008

(65) Prior Publication Data
US 2010/0166359 A1    Jul. 1, 2010

(30) Foreign Application Priority Data

Aug. 21, 2006  (JP) .................................. 2006-224546

(51) Int. Cl.
*G02B 6/00* (2006.01)
*G02B 6/34* (2006.01)

(52) U.S. Cl. ............................. 385/12; 385/36; 356/929

(58) Field of Classification Search ................. 385/12; 356/900, 928, 929
See application file for complete search history.

(56) References Cited

U.S. PATENT DOCUMENTS 7,406,222 B2 * 7/2008 Kornilovich ................... 385/30
2006/0234391 A1 * 10/2006 Weiss et al. ................... 436/518

FOREIGN PATENT DOCUMENTS

| JP | 6-58873 | 3/1994 |
| JP | 2002-148187 | 5/2002 |
| JP | 2002-195942 | 7/2002 |
| JP | 2004-170095 | 6/2004 |

(Continued)

OTHER PUBLICATIONS

Dong Ha Kim et al., An Optical Waveguide Study on the Nanopore Formation in Block Copolymer/Homopolymer Thin Films by Selective Solvent Swelling, The Journal of Physical Chemistry B 2006 110 (31), 15381-15388.*

(Continued)

*Primary Examiner* — Omar Rojas
(74) *Attorney, Agent, or Firm* — Ostrolenk Faber LLP

(57) ABSTRACT

A chip is constituted from a transparent substrate, a reflector film formed on the transparent substrate and an optical waveguide layer formed on the reflector film, and a plurality of pores is formed in the optical waveguide layer. A light-introducing mechanism that introduces light from the transparent substrate of the chip onto the reflector film, and a light-detecting mechanism that detects the light reflected on the reflector film are provided. A specimen under investigation is detected by sensing a change in the incidence angle or in the intensity of reflected light that occurs when the specimen is adsorbed or deposits on the surface of the optical waveguide layer, by using a range of incidence angles of the light in which the intensity of reflected light changes when a part or all of the incident light couples with the optical waveguide mode that propagates in the optical waveguide layer.

17 Claims, 15 Drawing Sheets

FOREIGN PATENT DOCUMENTS

| | | |
|---|---|---|
| JP | 2004-184381 | 7/2004 |
| JP | 2004-239715 A | 8/2004 |
| JP | 2005-195576 A | 7/2005 |
| JP | 2006-98263 A | 4/2006 |

OTHER PUBLICATIONS

International Search Report dated Sep. 21, 2007, issued in corresponding international application No. PCT/JP2007/061366.

Journal of Physical Chemistry B vol. 108, pp. 10, 812-10, 818, 2004.

* cited by examiner

CROSS SECTION OF CHIP WITH PORES FORMED THEREIN

RELATION BETWEEN THE INTENSITY OF REFLECTED LIGHT
AND THE INCIDENCE ANGLE OF LIGHT

INCIDENT LIGHT: P-POLARIZED LIGHT OF 633 nm
GLASS SUBSTRATE: REFRACTIVE INDEX 1.8
REFLECTOR FILM: GOLD HAVING A THICKNESS OF 47 nm
OPTICAL WAVEGUIDE: SILICA GLASS HAVING A THICKNESS OF 600 nm

INCIDENT LIGHT: S-POLARIZED LIGHT OF 300 nm
GLASS SUBSTRATE: REFRACTIVE INDEX 1.8
REFLECTOR FILM: CHROMIUM HAVING A THICKNESS OF 10 nm
OPTICAL WAVEGUIDE: SILICA GLASS HAVING A THICKNESS OF 300 nm

RELATION BETWEEN THE INTENSITY OF REFLECTED LIGHT
AND THE INCIDENCE ANGLE OF LIGHT

INCIDENT LIGHT: S-POLARIZED LIGHT OF 633 nm
GLASS SUBSTRATE: REFRACTIVE INDEX 1.8
REFLECTOR FILM: SILLICONE HAVING A THICKNESS OF 15 nm
OPTICAL WAVEGUIDE: SILICA GLASS HAVING A THICKNESS OF 600 nm

RELATION BETWEEN THE INTENSITY OF REFLECTED LIGHT
AND THE INCIDENCE ANGLE OF LIGHT

INCIDENT LIGHT: S-POLARIZED LIGHT OF 633 nm
GLASS SUBSTRATE: REFRACTIVE INDEX 1.8
REFLECTOR FILM: TUNGSTEN HAVING A THICKNESS OF 10 nm
OPTICAL WAVEGUIDE: SILICA GLASS HAVING A THICKNESS OF 600 nm

CHANGE IN INCIDENCE ANGLE DEPENDENCY OF INTENSITY OF REFLECTED LIGHT CAUSED BY SPECIFIC ADSORPTION OF STREPTOAVIDIN MEASURED BY USING SPECIMEN A

SHIFT IN INCIDENCE ANGLE WITH MINIMUM INTENSITY OF REFLECTED LIGHT:0.06°

CHANGE IN INCIDENCE ANGLE DEPENDENCY OF INTENSITY OF REFLECTED LIGHT CAUSED BY SPECIFIC ADSORPTION OF STREPTOAVIDIN MEASURED BY USING SPECIMEN B

SHIFT IN INCIDENCE ANGLE WITH MINIMUM INTENSITY OF REFLECTED LIGHT: 0.11°

CHANGE IN INCIDENCE ANGLE DEPENDENCY OF INTENSITY OF
REFLECTED LIGHT CAUSED BY SPECIFIC ADSORPTION OF STREPTOAVIDIN
MEASURED BY USING SPECIMEN C

SHIFT IN INCIDENCE ANGLE WITH MINIMUM INTENSITY OF
REFLECTED LIGHT: 0.35°

CHANGE IN INCIDENCE ANGLE DEPENDENCY OF INTENSITY OF
REFLECTED LIGHT CAUSED BY SPECIFIC ADSORPTION OF STREPTOAVIDIN
MEASURED BY USING SPECIMEN D

SHIFT IN INCIDENCE ANGLE WITH MINIMUM INTENSITY OF
REFLECTED LIGHT: 0.38°

CHANGE IN INCIDENCE ANGLE DEPENDENCY OF INTENSITY OF REFLECTED LIGHT CAUSED BY SPECIFIC ADSORPTION OF STREPTOAVIDIN MEASURED BY USING SPECIMEN E

SHIFT IN INCIDENCE ANGLE WITH MINIMUM INTENSITY OF REFLECTED LIGHT: 0.53°

OPTICAL WAVEGUIDE MODE SENSOR HAVING PORES

CROSS REFERENCE TO RELATED APPLICATIONS

The present application is a 35 U.S.C. §371 National Phase conversion of PCT/JP2007/061366, filed Jun. 5, 2007, which claims benefit of Japanese Application No. 2006-224546, filed Aug. 21, 2006, the disclosure of which is incorporated herein by reference. The PCT International Application was published in the Japanese language.

TECHNICAL FIELD

The present invention relates to an optical waveguide mode sensor and an optical waveguide mode sensor chip capable of improving the sensitivity of detecting a specimen by making use of an optical waveguide mode using an optical waveguide that has pores.

BACKGROUND ART

A technology is known that uses surface plasmon resonance (SPR) in a biosensor that detects DNA, proteins, sugar chains or the like, and a chemical substance sensor that detects metal ions, organic molecules or the like.

This technology employs a chip having such a structure as a glass plate is coated with a noble metal (gold, silver or the like) by vapor deposition, with the side of the glass opposite to the side coated with the metal put into contact with an optical prism via a refractive index matching oil, wherein a laser beam or white light is introduced through the prism into the glass and the intensity of the reflected light is measured.

The incident light irradiates the glass under a total reflection condition, and SPR occurs at a particular incidence angle due to an evanescent wave at the surface coated with the metal on the side opposite to the side where the light is incident.

When SPR occurs, the evanescent wave is absorbed by the surface plasmon, and therefore intensity of the reflected light decreases significantly around the incidence angle.

The intensity of reflected light at the incidence angle that induces SPR and at an angle near the incidence angle that induces SPR varies depending on the thickness and the relative dielectric constant of a material deposited on the metal surface. A conventional SPR sensor makes use of this effect to determine the extent of coupling (film thickness or weight) of the specimen under investigation, by modifying a material that couples with or is adsorbed on the specimen on the surface of a metal and detecting the change in the incidence angle or reflectivity caused by the coupling or adsorption of the specimen in the vicinity of the metal surface.

Applications of the technology based on SPR include those disclosed in Patent Document 1 "Optical sensor, detection method using optical sensor and formation of molecular recognizing film for optical", Patent Document 2 "Sensor utilizing Attenuated total reflection", Patent Document 3 "Optical waveguide type SPR measurement chip, method for manufacturing the same and SPR measuring method", Patent Document 4 "Waveguide structure, its manufacturing method, and surface Plasmon resonance sensor and refractive index change measurement method using the waveguide structure", and Patent Document 5 "Optical waveguide type surface plasmon resonance sensor and optical waveguide type surface plasmon resonance device".

However, the prior art technologies that utilize the surface plasmon resonance described above have the problem that the sensitivity is not enough to detect a small specimen.

An attempt to overcome this drawback by using an optical system similar to the SPR sensor has been reported (Non-Patent Document 1), according to which molecules adsorbed on a sensor surface can be measured with high sensitivity by forming an optical waveguide on the surface of a noble metal of the SPR sensor and utilizing an optical waveguide mode excited in the optical waveguide.

The optical waveguide mode is caused by multiple reflections within a dielectric material. FIG. 1 shows a substrate structure of a chip that demonstrates an optical waveguide mode.

Light incident on a glass at an angle passes through the glass and illuminates a reflector layer so as to generate an evanescent wave on the side of a dielectric optical waveguide. When the evanescent wave couples with the optical waveguide mode in the dielectric optical waveguide, a part or all of the incident light propagates in the dielectric optical waveguide and is therefore not reflected. Thus coupling of the incident light with the optical waveguide mode in the dielectric optical waveguide causes a decrease in the intensity of reflected light. This decrease in the intensity of the reflected light occurs only at incidence angles near a particular angle for the light of a given wavelength.

The particular incidence angle and the intensity of reflected light at the incidence angle depend greatly on the relative dielectric constant of the surface of the dielectric optical waveguide. As a result, when a substance is adsorbed, deposits or otherwise attaches to the surface of the dielectric optical waveguide, the incidence angle and the intensity of reflected light change. The conventional optical waveguide mode sensor measures this change to determine the presence of a particular substance and the quantity of the substance.

Sensitivity of the optical waveguide mode sensor can be improved by increasing the surface area of the optical waveguide. Non-Patent Document 1 describes that high-sensitivity sensing can be achieved by using alumina that is formed by anodic oxidation as the optical waveguide. However, it is difficult to control the size of pores formed in alumina, and alumina is not stable in the presence of acid or alkali. Moreover, it may not be easy to modify a substance that couples with or adsorbs a specimen on the surface thereof.

Patent Document 1: Japanese Unexamined Patent Application, First Publication No. 6-58873

Patent Document 2: Japanese Unexamined Patent Application, First Publication No. 2002-195942

Patent Document 3: Japanese Unexamined Patent Application, Application No. 2000-339895

Patent Document 4: Japanese Unexamined Patent Application, First Publication No. 2004-170095

Patent Document 5: Japanese Unexamined Patent Application, First Publication No. 2004-184381

Non-Patent Document 1: Journal of Physical Chemistry B Vol. 108, pp. 10,812-10,818, 2004

DISCLOSURE OF INVENTION

Means for Solving the Problems

The present invention aims at solving the problems described above, and provides a optical waveguide mode sensor that uses an optical waveguide made of an optical waveguide material which is stable and easy to process with pores formed therein, and is capable of detecting, free of labeling, smaller specimens quickly with a sensitivity higher than that of the prior art technology that utilizes the optical waveguide mode, and also provides a chip for the sensor.

The optical waveguide mode sensor of the present invention uses a chip that comprises a substrate made of a transparent dielectric material or a transparent electrically-conductive material, a reflector film formed thereon and an optical waveguide layer formed on the reflector film. A plurality of pores is formed in the optical waveguide layer so as to penetrate therethrough, and there is provided a light-introducing mechanism that introduces light from the substrate side of the chip onto the reflector film and a light-detecting mechanism that detects the light reflected on the reflector film. A specimen is detected by sensing a change in the incidence angle or in the intensity of reflected light that occurs when the specimen is adsorbed or deposits on the surface of the optical waveguide layer, by using a range of incidence angles in which the intensity of reflected light changes when a part or all of the incident light couples with the optical waveguide mode that propagates in the optical waveguide layer. The optical waveguide layer has a thickness in a range from 60 nm to 1 μm. The pores are formed such that the total area of the inner wall surfaces of the pores, or the increase in the surface area caused by forming the pores, is in a range from 0.1 $cm^2$ to 280 $cm^2$ per 1 $cm^2$ of the surface area of the optical waveguide.

The reflector film is a thin metal film of one or more components selected from among the metals of Groups 4 to 14 of the Periodic Table and alloys of these metals.

The reflector film is a thin film of a semiconductor material. The semiconductor material may be a semiconductor consisting of a single element such as Si or Ge or a compound semiconductor, and the type of conductivity thereof may be either n type, p type or intrinsic semiconductor.

The optical waveguide layer has such a film thickness that allows the optical waveguide mode to be induced.

A molecular recognition group is chemically modified on the surface of the optical waveguide layer. Any one of an amino group, a hydroxyl group, a carboxyl group, an aldehyde group, an isothiocyanate group, a succinimide group, a biotinyl group, a methyl group and a fluoromethyl group is chemically modified as the molecular recognition group. Any molecular recognition group described above is preferably used without any limitation.

The incident light is p-polarized or s-polarized, and reflection of the light is detected. The substrate may have a plate configuration. The substrate surface on the side opposite to the surface where the optical waveguide layer of the chip is formed is put into contact with an optical prism via the refractive index matching oil. The substrate may be a prism.

When p-polarized or s-polarized light enters the optical prism at an incidence angle with respect to the center axis of the prism, the incidence angle of the light is fixed proximate to the incidence angle at which the intensity of reflected light changes, and the intensity of reflected light is measured. Measurement is made on the film thickness, weight, size or relative dielectric constant of a molecule, an ion or a cluster of molecules that is selectively adsorbed by or chemically bonds with a molecular recognition group that is chemically modified on the surface of the optical waveguide layer, in a gas or liquid.

The optical waveguide mode sensor of the present invention uses a chip for an optical waveguide mode sensor to detect a specimen by making use of the optical waveguide mode of the optical waveguide of the chip.

Effects of the Invention

The present invention has remarkable effects of easily producing a sensor that has high sensitivity and high stability, by using an optical waveguide formed mainly from silicon oxide that can be easily machined and is chemically stable, an optical waveguide formed mainly from titanium oxide, or an optical waveguide formed from an organic material, glass, a polymer or a transparent electrically-conductive material, where these optical waveguides have a thickness from 60 nm to 1 μm that is optimum for a microscopic machining process, and forming pores in the optical waveguide. Moreover, an excellent effect of improving the sensitivity of detecting the specimen under investigation can be achieved by employing selective etching based on ion implantation as a machining method and using the optical waveguide mode in the optical waveguide that has the pores. In addition, such a remarkable effect can be achieved that it is made possible to quickly detect, without using a label, a smaller specimen with a sensitivity higher than that of the prior art technology that utilizes the surface plasmon resonance.

BEST MODE FOR CARRYING OUT THE INVENTION

Now the present invention will be described with reference to the accompanying drawings. The description that follows is intended to help better understand the present invention, and is not intended to restrict the present invention. Accordingly, modifications, embodiments and other examples based on the technological concept of the present invention are included in the present invention.

Figure 1:
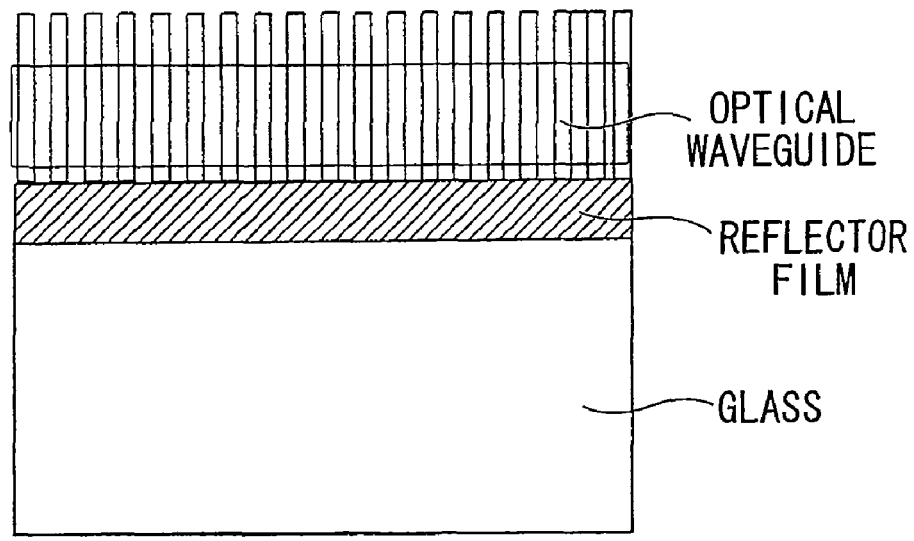
FIG. 1 shows a chip structure in which an optical waveguide mode is induced.

As described above, the present invention uses an optical waveguide mode for improving the sensitivity. FIG. 1 shows a substrate that develops the optical waveguide mode used in the present invention, namely the structure of a chip for a optical waveguide mode sensor. The chip shown in FIG. 1 has a structure having pores formed therein. The optical waveguide mode sensor chip illustrated has a reflector film formed on the top surface of a glass substrate, and an optical waveguide formed thereon, where the pores that penetrate the optical waveguide layer are formed. When light enters from the side of glass where the optical waveguide of the chip is not formed under particular conditions, a part or all of the incident light propagates in the optical waveguide. The description that follows takes a case of using a glass substrate as an example, although the substrate may be formed from, besides glass, a transparent dielectric material such as plastic (resin), ceramic or insulator or a transparent electrically-conductive material such as ITO.

As light is introduced from the glass side into the chip having the structure described above, intensity of the reflected light changes sharply when the incidence angle takes a particular value. A typical example where the reflected light shows a sharp decrease will be described below with reference to FIG. 2.

Figure 2:
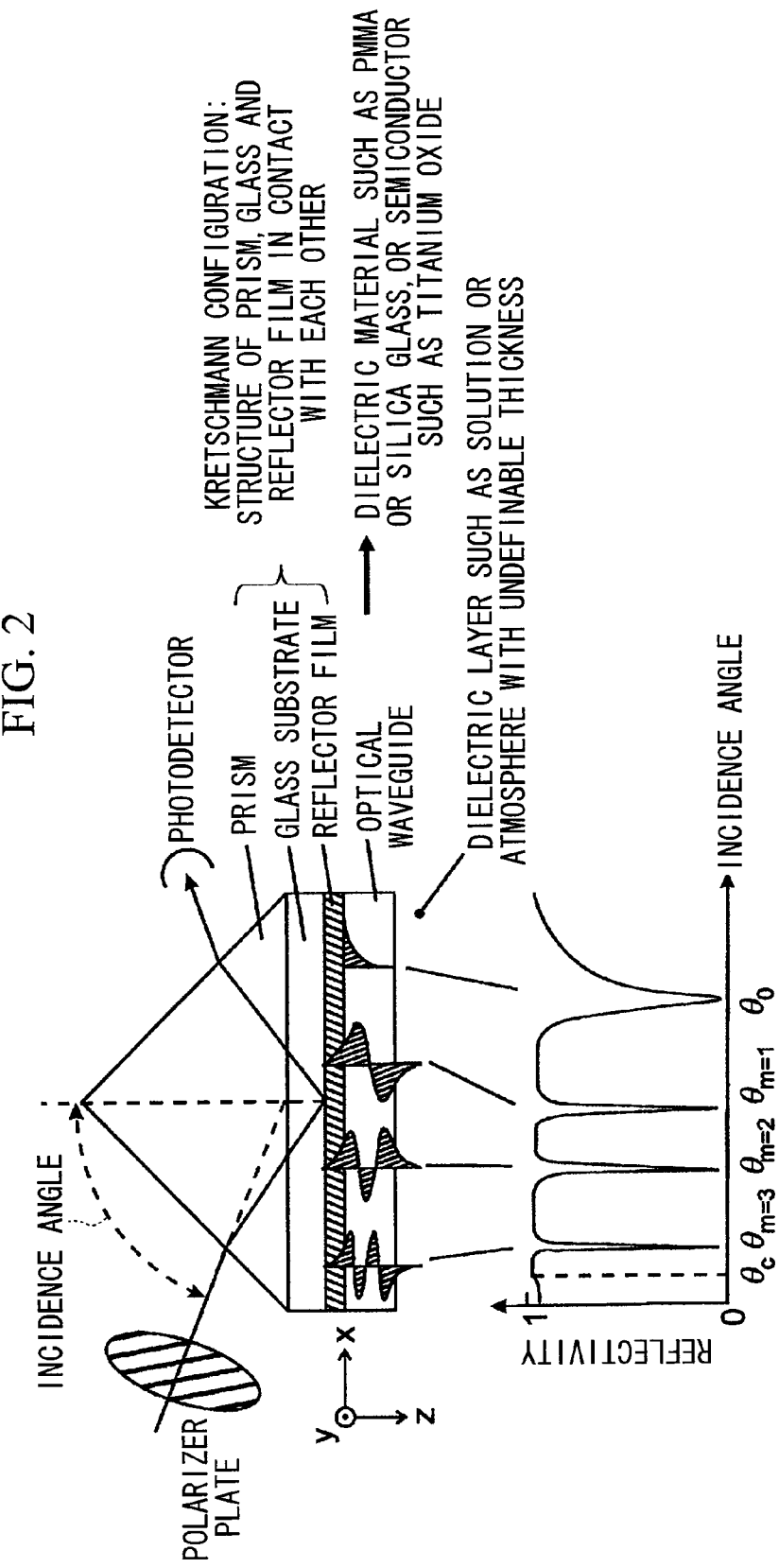
FIG. 2 shows an example of the optical setup for inducing the optical waveguide mode.

FIG. 2 shows a relation between the intensity of reflected light and the incidence angle of light when the light is incident on a setup having a prism disposed on the glass side of the chip shown in FIG. 1, namely on the side where the optical waveguide is not formed. The graph of FIG. 2 shows four decreases, or dips, in the intensity of reflected light. Such decreases in the intensity of reflected light result from mainly two causes. One is the surface plasmon resonance described previously, and the dip in the intensity of reflected light taking place at an incidence angle $\theta_0$ in FIG. 2 is caused by the surface plasmon resonance. The surface plasmon resonance occurs when a metal having a negative relative dielectric constant, especially a noble metal, is used as the reflector film, even when there is no optical waveguide. The decrease in the reflected light due to the surface plasmon resonance occurs when the incident light is p-polarized, but does not occur when the incident light is s-polarized.

Other decreases in the intensity of reflected light shown in FIG. 2 are due to the optical waveguide mode, and correspond to the dips at incidence angles $\theta_{m=1,2,3}$. These types of dips in the intensity of reflected light do not occur when there is no optical waveguide shown in FIG. 1, or when this layer is thin. The minimum thickness of the optical waveguide layer that allows the optical waveguide mode to develop, while depending on the polarization state of the light, may be thin when these layers have a high refractive index, or when the light has a short wavelength. In contrast, when these layers have a low refractive index or when the light has a long wavelength, thicker layers are required. For example, when the optical waveguide layer has refractive index of about 1.75 and s-polarized light in the visible region is used, the optical waveguide mode occurs in the optical waveguide layer that has a thickness of about 60 nm or larger.

The optical waveguide mode represents the state of propagation of light that is confined within a limited space. The most well-known optical waveguide mode is the state of propagation of light within an optical fiber. An optical fiber comprises a fiber (generally referred to as a core) having a high refractive index running at the center of a cladding (generally having a very long and narrow cylindrical form) having a low refractive index. Light is confined within the core and propagates therein due to reflection of the light caused by the difference in the refractive index.

A slab type optical waveguide is also well known, in which light propagates in a sheet-shaped material sandwiched by a material having a low refractive index (including air and a vacuum).

The chip used in the present invention has such a structure as shown in FIG. 1, wherein a glass substrate has a reflector film formed thereon, and an optical waveguide layer is formed further thereon. When the top (surface side) of the optical waveguide layer makes contact with a material that has a refractive index lower than that of this layer, such as air or water, the layer takes a structure resembling that of a slab type optical waveguide, being capable of confining light within the layer and causing the light to propagate therein. The state of light being confined within this layer and propagating therein is the optical waveguide mode used in the present invention.

In the case light is incident on the glass side of the setup shown in FIG. 1 where the reflector film is relatively thin, a part or all of the light leaks as an evanescent wave to the optical waveguide side even when the light irradiates with an incidence angle that satisfies the total reflection condition. When the incidence angle of the light takes a particular value, the evanescent wave propagates in the optical waveguide. This phenomenon is expressed as the incident light couples with the optical waveguide mode, or the incident light takes the optical waveguide mode. When this occurs, a part or all of the incident light propagates in the optical waveguide and is therefore not reflected. As a result, the intensity of reflected light decreases as described previously. This decrease in the intensity of reflected light occurs only at incidence angles near a particular angle for the light of a given wavelength, exhibiting a dip profile as shown in FIG. 2.

The example described above is a case where the dip is observed as a result of decreasing intensity of the reflected light. In contrast, there may be such a case as the incident light couples with the optical waveguide mode, which results in an increase in the intensity of reflected light. In this case, light incident at such an angle that does not cause coupling with the optical waveguide mode has a low intensity of reflected light, while light incident at such an angle that causes coupling with the optical waveguide mode has a high intensity of reflected light.

The constitution shown in FIG. 2, which is called the Kretschmann configuration (a structure consisting of a prism, a glass plate and a reflector film that are in contact with each other) is used in the conventional optical systems of surface plasmon resonance. In the optical waveguide mode sensor of the present invention, an optical waveguide is added to the reflector film surface. When light is introduced through a polarizer plate and the prism to enter on the glass side to the reflector film, the incident light couples with the optical waveguide mode of the optical waveguide under particular conditions, thus resulting in a change in the intensity of reflected light as described above. Intensity of light reflected by the reflector film is detected by a detector.

Figure 3:
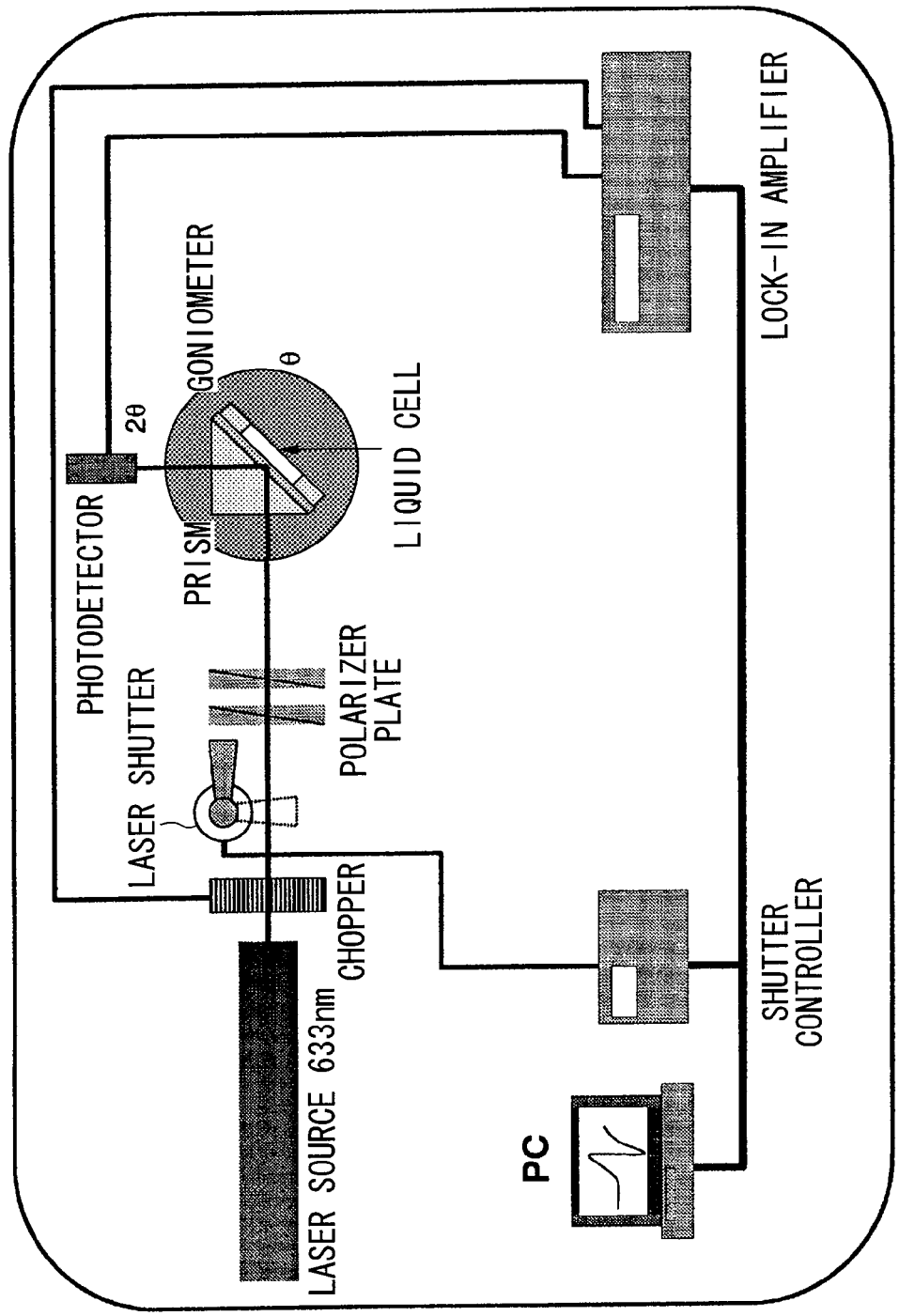
FIG. 3 shows an example of the constitution of an optical waveguide mode sensor.

FIG. 3 shows an example of the constitution of an optical waveguide mode sensor system, which usually comprises a laser source, a laser shutter and a controller thereof, a polarizer plate, a goniometer, a light detector and analysis software (PC). A setup comprising a liquid cell, a chip and a prism are placed on the goniometer that controls the incidence angle, p- or s-polarized laser light is introduced through the polarizer plate into the prism. Reflection of this light is introduced into a photodetector. The liquid cell is used to hold a solution to be detected on the molecule detection surface of the chip, namely on the surface of the optical waveguide. A chopper and a lock-in amplifier may be used to suppress the noise generated by extraneous light (such as room light) other than the laser beam.

The polarizer plate is often used in a set of two plates as shown in FIG. 3, in which case the polarizer plate that is located nearer to the prism among the two polarizer plates is provided for the purpose of selecting p-polarization that oscillates in a plane parallel to the reflector surface or s-polarization that oscillates in a plane perpendicular to the reflector surface. The polarizer plate that is located nearer to the laser source is provided for regulating the intensity of light introduced into the optical waveguide.

Thus the change in the intensity of reflected light due to the optical waveguide mode can be detected with an optical system similar to the Kretschmann configuration. Therefore, the present invention employs this optical system. The optical prism may be of any type such as a cylindrical prism or a semi-sphere prism, as well as the triangular prism shown in the diagram. The optical prism has a function of changing the incidence angle at which the incident light couples with the optical waveguide mode.

Now examples of various characteristics of reflected light due to the coupling of the optical waveguide mode and the incident light will be described.

Figure 4:
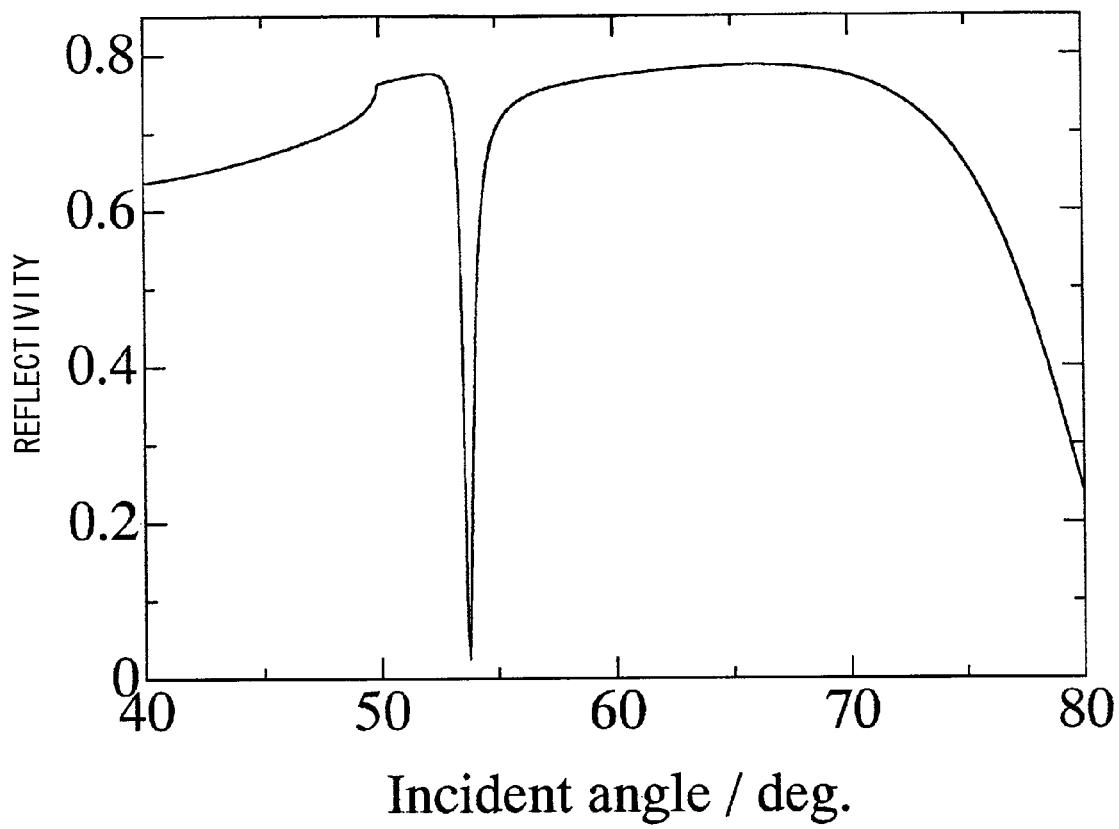
FIG. 4 is a graph showing a relation between the intensity of reflected light and the incidence angle of light when p-polarized light of 633 nm is incident on a device that uses a glass substrate having a refractive index of 1.8, a reflector film formed from gold having a thickness of 47 nm and an optical waveguide formed from silica glass having a thickness of 600 nm.

The most well-known behavior is such a phenomenon that the intensity of the reflected light decreases sharply when the incidence angle takes a particular value. An example of this phenomenon is shown in FIG. 4. FIG. 4 is a graph showing the relation between the intensity of reflected light and the incidence angle of light when p-polarized light of 633 nm is incident on a device that uses a glass substrate having a refractive index of 1.8, a reflector film formed from gold having a thickness of 47 nm and an optical waveguide formed from silica glass having a thickness of 600 nm. Silica glass is one type of the most stable silicon oxide. It is assumed here that the surface of the optical waveguide layer is immersed in water. As can be seen from FIG. 4, intensity of reflected light decreases (dips) sharply at a particular incidence angle of 53.8°.

Figure 5:
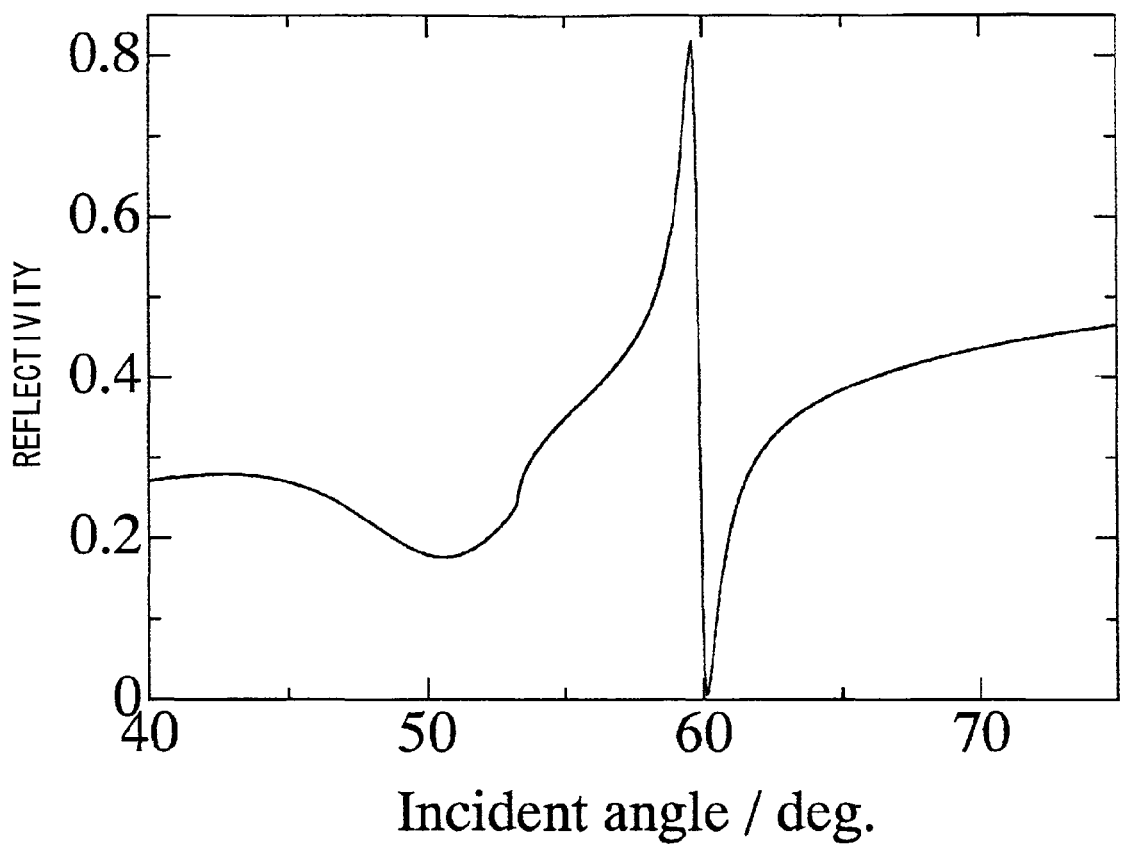
FIG. 5 is a graph showing a relation between the intensity of reflected light and the incidence angle of light when s-polarized light of 300 nm is incident on a device that uses a glass substrate having a refractive index of 1.8, a reflector film formed from chromium having a thickness of 10 nm and an optical waveguide formed from silica glass having a thickness of 300 nm.

There may also occur such a phenomenon that the intensity of reflected light increases at a particular incidence angle and decreases sharply at another angle near the former incidence angle. An example of this phenomenon is shown in FIG. 5. FIG. 5 is a graph showing the relation between the intensity of reflected light and the incidence angle of light when s-polarized light of 300 nm is incident on a device that uses a glass substrate having a refractive index of 1.8, a reflector film formed from chromium having a thickness of 10 nm and an optical waveguide formed from silica glass having a thickness of 300 nm. It is assumed that the surface of the optical waveguide layer is immersed in water also in this case. As can be seen from FIG. 5, the intensity of reflected light increases in a region of incident angles lower than 59.9°, and the intensity of reflected light decreases in a region of higher angles.

Figure 6:
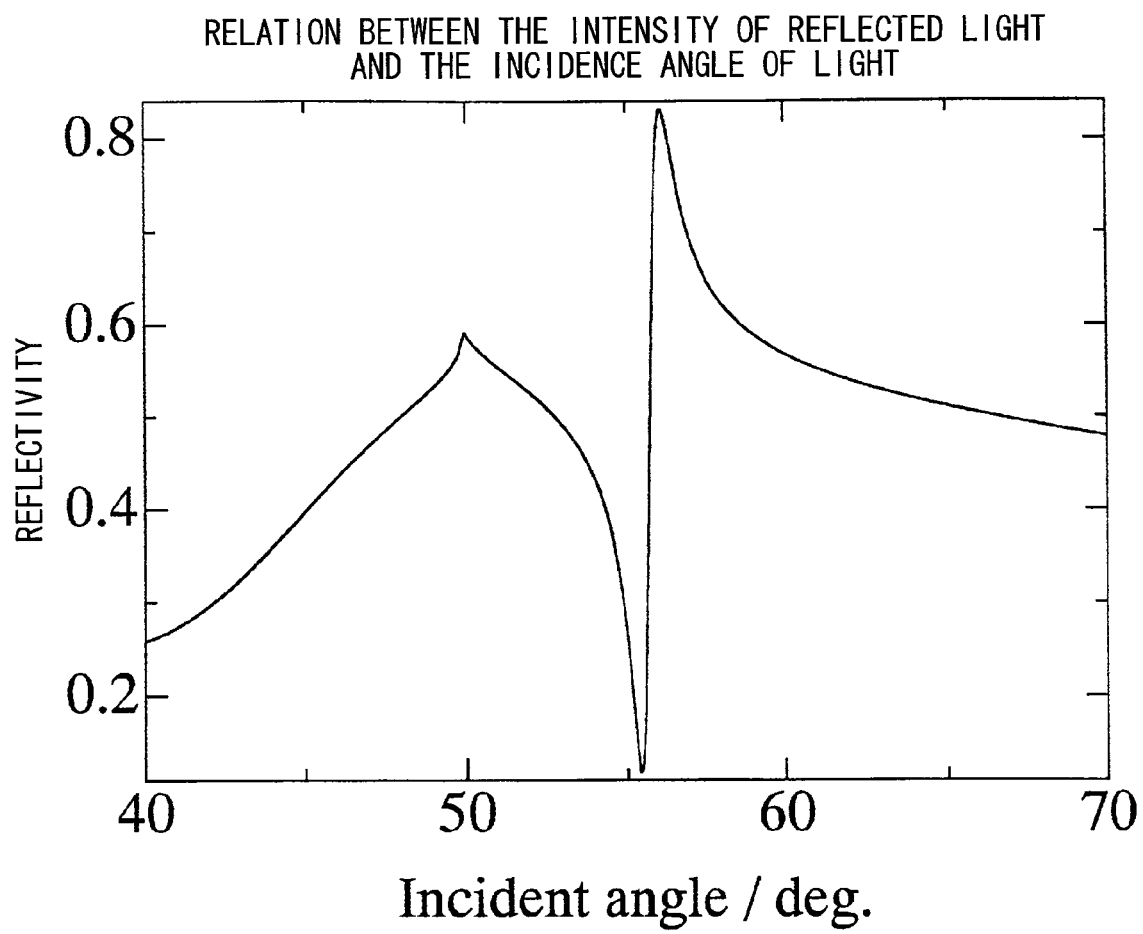
FIG. 6 is a graph showing a relation between the intensity of reflected light and the incidence angle of light when s-polarized light of 633 nm is incident on a device that uses a glass substrate having a refractive index of 1.8, a reflector film formed from silicon having a thickness of 15 nm and an optical waveguide formed from silica glass having a thickness of 600 nm.

There may also occur such a case that resembles that of the case of chromium, but the intensity of reflected light changes oppositely with the incidence angle. An example of this phenomenon is shown in FIG. 6. FIG. 6 is a graph showing the relation between the intensity of reflected light and the incidence angle of light when s-polarized light of 633 nm is incident on a device that uses a glass substrate having a refractive index of 1.8, a reflector film formed from silicon having a thickness of 15 nm and an optical waveguide formed from silica glass having a thickness of 600 nm. Also in this case, it is assumed that the surface of the optical waveguide layer is immersed in water. As can be seen from FIG. 6, the intensity of reflected light decreases in a region of incident angles lower than 55.7°, and the intensity of reflected light increases in a region of higher angles, in contrast to the case shown in FIG. 5.

Figure 7:
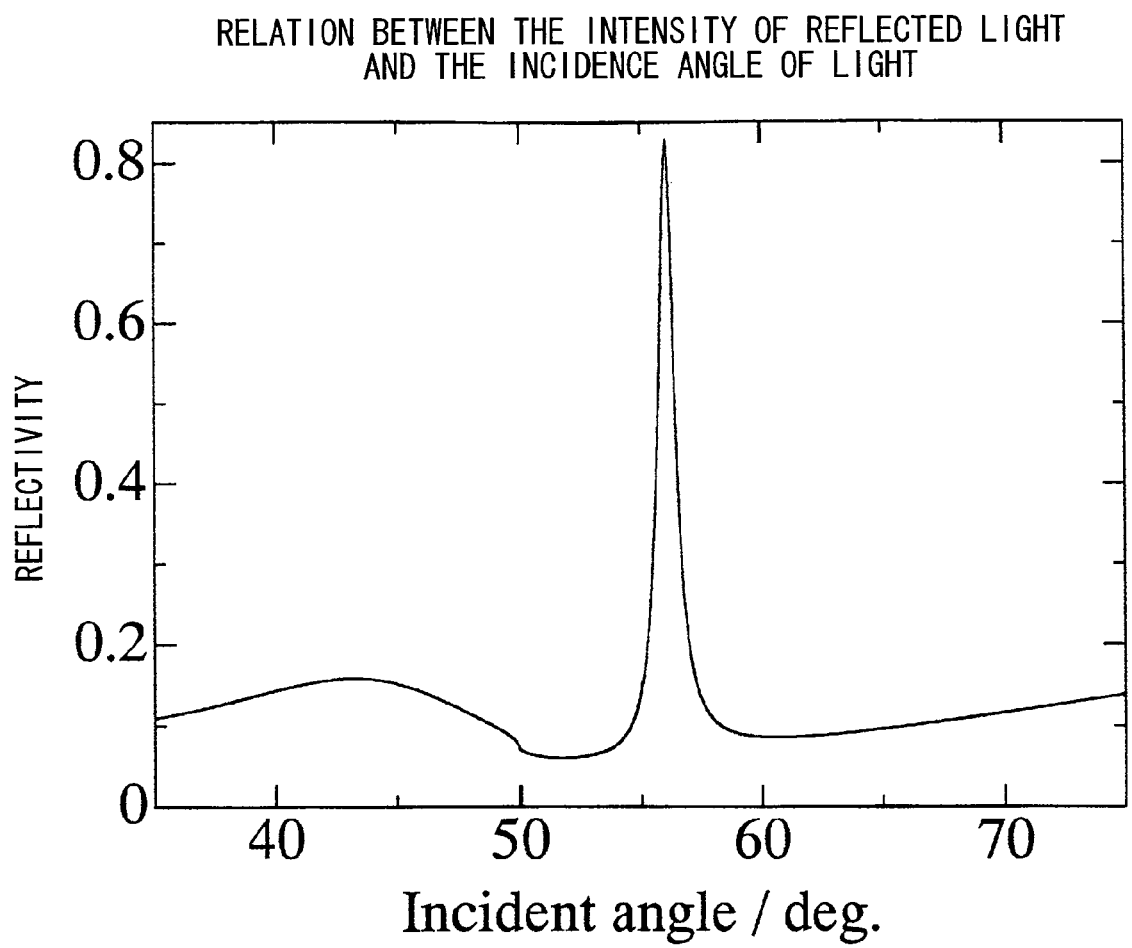
FIG. 7 is a graph showing a relation between the intensity of reflected light and the incidence angle of light when s-polarized light of 633 nm is incident on a device that uses a glass substrate having a refractive index of 1.8, a reflector film formed from tungsten having a thickness of 10 nm and an optical waveguide formed from silica glass having a thickness of 600 nm.

There may also occur such a case that the intensity of reflected light increases sharply at a particular incidence angle. An example of such a case is shown in FIG. 7. FIG. 7 is a graph showing the relation between the intensity of reflected light and the incidence angle of light when s-polarized light of 633 nm is incident on a device that uses a glass substrate having a refractive index of 1.8, a reflector film formed from tungsten having a thickness of 10 nm and an optical waveguide formed from silica glass having a thickness of 600 nm. It is assumed that the surface of the optical waveguide layer is immersed in water also in this case. As can be seen from FIG. 7, the intensity of reflected light increases sharply at angles near 56.1°.

In this way, the intensity of reflected light shows significant changes when the incident light couples with the optical waveguide mode of the optical waveguide.

The number of optical waveguide modes is not limited to one, and varies depending on the wavelength of light that propagates, state of polarization and thickness and refractive index of the optical waveguide layer. In general, the optical waveguide mode does not appear in an optical waveguide layer that is very thin. While the optical waveguide mode appears as the optical waveguide layer becomes thicker, the optical waveguide layer having a low refractive index must be thicker to have optical waveguide mode. The optical waveguide mode appears in a relatively thin optical waveguide layer when the refractive index is high. While the optical waveguide mode appears as the thickness of the optical waveguide layer is increased, the optical waveguide mode that appears first is called the 1st optical waveguide mode, the optical waveguide mode that appears next as the thickness is increased is called the 2nd optical waveguide mode, and so on. As the thickness increases, more optical waveguide modes appear such as 3rd and 4th.

Thus as the optical waveguide becomes thicker, the intensity of reflected light first shows a change due to the coupling of the 1st optical waveguide mode and the incident light. As the optical waveguide becomes further thicker, the intensity of reflected light shows a change due to the coupling of the 2nd optical waveguide mode and the incident light. As the optical waveguide becomes further thicker, the intensity of reflected light shows a change due to the coupling of the optical waveguide mode of a higher order and the incident light.

The intensity of reflected light changes significantly due to the coupling of the optical waveguide mode and the incident light, as described previously. The angle at which the intensity of reflected light changes significantly and the intensity of the reflected light are heavily affected by the change in the relative dielectric constant of the optical waveguide surface. As a result, when a substance is adsorbed, deposited or otherwise attaches to the optical waveguide surface, the angle and intensity of the reflected light change. The optical waveguide mode sensor of the present invention senses this change to determine the presence of a particular substance and the quantity of the substance.

This sensor may also be used as a sensor for evaluating the physical properties of a thin film, since it is capable of measuring the thickness, refractive index and relative dielectric constant of the thin film that is formed on the optical waveguide surface.

The substrate is preferably formed from a material that has a refractive index roughly in a range from 1.4 to 2.2, more preferably from 1.6 to 2.0 for the light used in the detecting operation.

Silicon oxide is a preferable material to be used in the optical waveguide, since it has such advantages as ease of depositing on the reflector film, ease of machining, chemical stability, capability to form an optically smooth surface, inertness with regard to bio-related substances, and ease of chemical modification of the surface. Silicon oxide may be deposited by a sol-gel method, a thermal oxidation process, sputtering or the like. Besides silicon oxide, a metal oxide such as titanium oxide, a polymer such as polymethyl-methacrylate, an organic substance, glass or a transparent electrically-conductive material is also preferably used for similar reasons.

The pores of the optical waveguide layer may be formed by chemical etching using a solution that dissolves the material forming the optical waveguide, or dry etching such as reactive ion etching. The most common method of forming the pores is to coat the optical waveguide surface with a resist, form a dot pattern on the resist by lithography and form the pores by chemical etching or dry etching. In the case the optical waveguide itself is formed from a resist, the optical waveguide having the pores is obtained at the time the resist is subjected to a development process after forming the dot pattern by lithography. The pores may not necessarily be formed in true circles, and may have an oval or a polygonal shape. It is not necessary to form the pores in a size constant along the depth, and the diameter may increase or decrease along the depth.

Lithography is generally advantageous for forming a regular pattern, although the arrangement of the pores in the present invention may be irregular. Random arrangement of the pores may be formed very effectively by combining the implantation of ions into the optical waveguide material with chemical etching conducted after the ion implantation. When ions are accelerated with a high energy and implanted into silicon oxide, titanium oxide, a polymer, an organic substance, glass or a transparent electrically-conductive material, the portions where the ions have passed through turn into a state that can undergo selective chemical etching. For example, when ions are accelerated with an energy of MeV order and are implanted into silicon oxide or titanium oxide followed by etching with a solution or vapor of hydrofluoric acid or hydroborofluoric acid, the portion irradiated with the ions is etched more efficiently than the portion that is not irradiated with the ions, thus making it possible to form pores of very small diameter. The pores are preferably formed with a diameter not larger than the wavelength of the light that is used. This is because pores larger than the wavelength of the light cause interference of the light, which makes the analysis of sensing data complicated.

The thickness of the optical waveguide layer is preferably not less than 60 nm and not larger than about 1 μm. As described previously, a thickness of such a level enables changes in the intensity of reflected light caused by the optical waveguide mode to be satisfactorily observed. Making the optical waveguide layer thicker results in a longer time required to form the optical waveguide and increases the possible error in thickness of the layer to be formed.

In order to achieve higher sensitivity by forming the pores, it is preferable to form a large number of pores and achieve a greater increase in the surface area. The increase in surface area brought about by forming the pores can be determined by summing up the areas of the inner walls of the pores. When the pores have a cylindrical shape, the increase in surface area ($\chi$, per unit surface area) is given as $\chi=2\pi r \times h \times n$ (r is the radius of the pores, h is the depth of the pores, and n is the number of pores per unit surface). The proportion of the surface area of the optical waveguide occupied by the pores (surface area occupation ratio, k %) is given as $k=100\times\pi r^2 n$. Accordingly, the increase in surface area can be expressed as $\chi=2hk/100r$.

There are limitations on the size and the number of pores that can be formed in the optical waveguide surface. The lower limit of radius r of the pores that can be formed easily with the processes described above is about 5 nm. And it is not practical to form the pores with a surface area occupation ratio higher than 70%, since it is necessary to control the pore diameter and the layout of the pores very strictly. The upper limit of the preferable thickness of an optical waveguide layer is 1 μm as described previously. Thus the maximum depth of the pores that can be formed in the film is the depth of the pore that penetrates the film, namely 1 μm. Accordingly, the maximum increase in the surface area per 1 $cm^2$ of the optical waveguide that can be practically achieved is about 280 $cm^2$. It is not practical to obtain a greater increase in surface area, since it is necessary to employ a too complicated process and this leads to an expensive sensor. As will be described later, the minimum increase in the surface area is about 0.1 $cm^2$. Thus it is preferable to select the radius and the number of pores such that the increase in the surface area is not less than 0.1 $cm^2$ and not larger than 280 $cm^2$. It is desirable to form the pores as deep as possible, and therefore the pores preferably penetrate through the optical waveguide layer.

In practice, it is assumed that pores that can be readily formed with the current technology are limited to about 10 nm in radius, 1 μm in depth and about 50% in surface area occupation ratio. Thus in practice, it is preferable to select the radius and the number of pores such that the increase in the surface area per 1 $cm^2$ of the optical waveguide is not larger than 100 $cm^2$.

When ions are implanted into the silicon oxide film followed by etching with a vapor of a hydrofluoric acid to form the pores, the minimum radius of the pores that can be formed is about 15 nm. Pores having a depth up to about 800 nm can be readily formed. With this technique, since the pores are formed at randomly distributed positions, an attempt to increase the surface area occupation ratio may cause some of the pores to be combined with each other into a larger pore. The upper limit of the surface area occupation ratio that is readily obtained is about 30%. Therefore, when forming the pores with this process, it is preferable to select the radius and the number of pores such that the increase in the surface area per 1 $cm^2$ of the optical waveguide is not larger than about 32 $cm^2$.

A thickness of about 500 nm is enough for the optical waveguide layer to achieve a change in the intensity of reflected light caused by the optical waveguide mode. And 20% to 21% is considered to be sufficient for the surface area occupation ratio. Thus it is concluded that a sensor having a satisfactory sensitivity can be made by forming the pores with an increase of about 14.5 cm$^2$ or less in the surface area per 1 cm$^2$ of the optical waveguide.

The reflector film, among materials that are chemically and physically stable, may be formed from a metal selected from among elements of Groups 4 to 14 of the Periodic Table and alloys of these metals. A semiconductor material may also be preferably used. In the case a semiconductor material is used, either a single-element semiconductor material such as Si or Ge or a compound semiconductor may be used. The type of conductivity of the semiconductor may also be p-type, s-type or insulating (intrinsic). While there is no restriction on the light used in the detection as long as it is an electromagnetic wave, it is preferable to use light in the infrared region to the ultraviolet region, since the light such advantages as ease of use.

EXAMPLES

Chips were fabricated by coating one side of a glass plate measuring 25 mm square and 1 mm in thickness having a refractive index of 1.77 with chromium (0.8 nm), gold (47 mm) and chromium (0.8 nm) in this order by vacuum deposition, and forming a silicon oxide film of about 500 nm by sputtering method. This silicon oxide layer constitutes the optical waveguide. Chromium is used for the purpose of improving the bonding strength between gold and glass, and between gold and the silicon oxide optical waveguide layer. Silicon oxide was subjected to a heat treatment at 600° C. for 24 hours after being deposited. The heat treatment was conducted in order to increase the density of silicon oxide. Five chips were made, of which four were subjected to ion implantation and etching with the pores being formed therein thereafter. Au ions were used in the ion implantation to irradiate the optical waveguide layer with ions accelerated by an energy of 137 MeV. The dose of ions was set to $5 \times 10^8$, $3 \times 10^9$, $5 \times 10^9$ and $7 \times 10^9$ ions per 1 cm$^2$. Etching was carried out by using a vapor of hydrofluoric acid. The pore diameter was varied by controlling the etching time. The chip prepared without ion implantation and etching is called specimen A, and the chips prepared by implantation of $5 \times 10^8$, $3 \times 10^9$, $5 \times 10^9$ and $7 \times 10^9$ ions and etching are called specimen B, specimen C, specimen D and specimen E, respectively.

Figure 8:
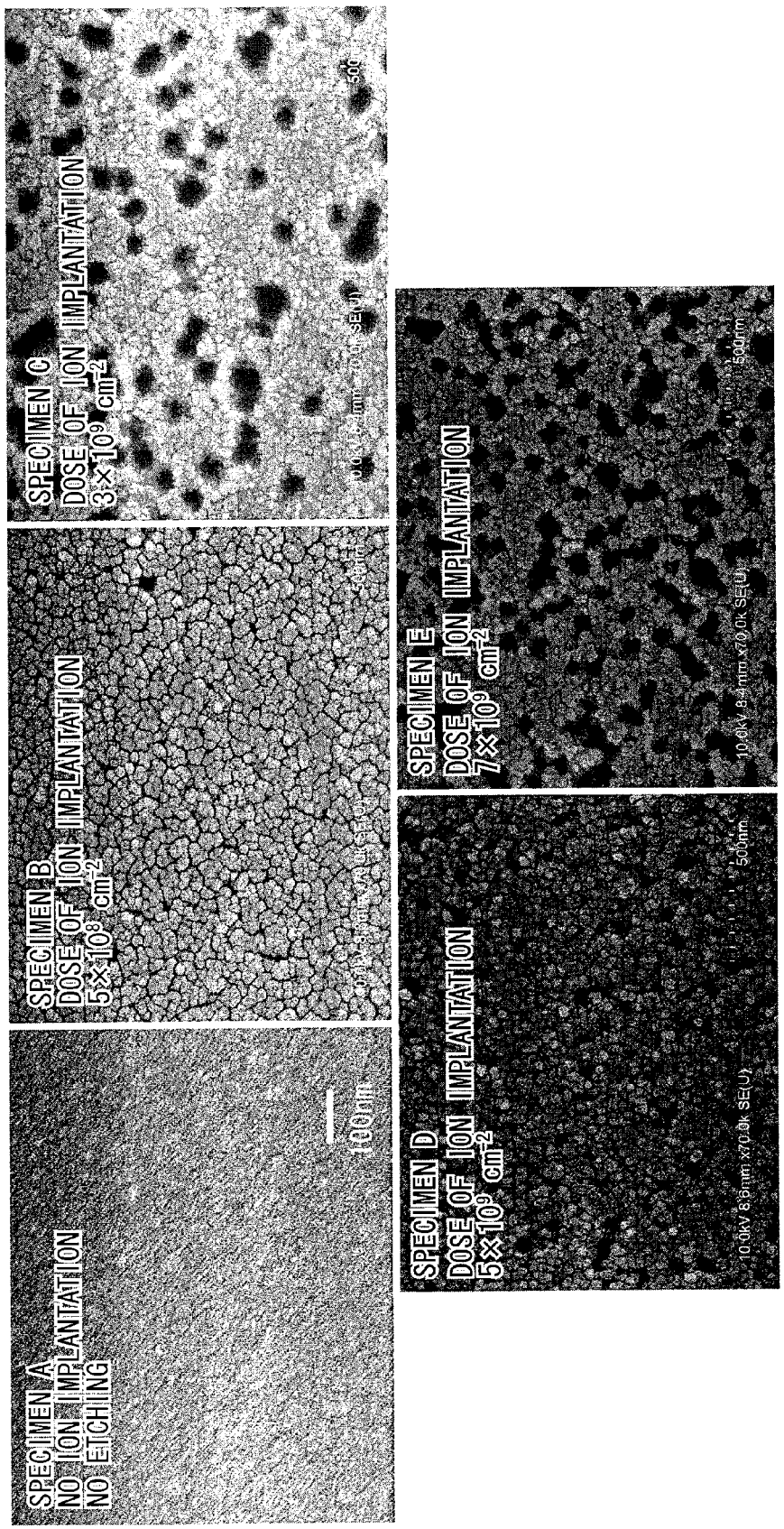
FIG. 8 shows electron microscope photographs of specimens A, B, C, D, E prepared in Examples.

Electron microscope photographs of the surfaces of the five chips prepared by the process described above are shown in FIG. 8. The specimen A has a very smooth surface. It can be seen that pores are formed in the specimens B, C, D and E, and the mean radius of the pores was 15 nm, 29 nm, 16 nm and 27 nm, respectively.

A part of the silicon oxide layer was broken to observe the pores, and it was verified that the pores penetrated through the silicon oxide layer in all specimens.

Figure 9:
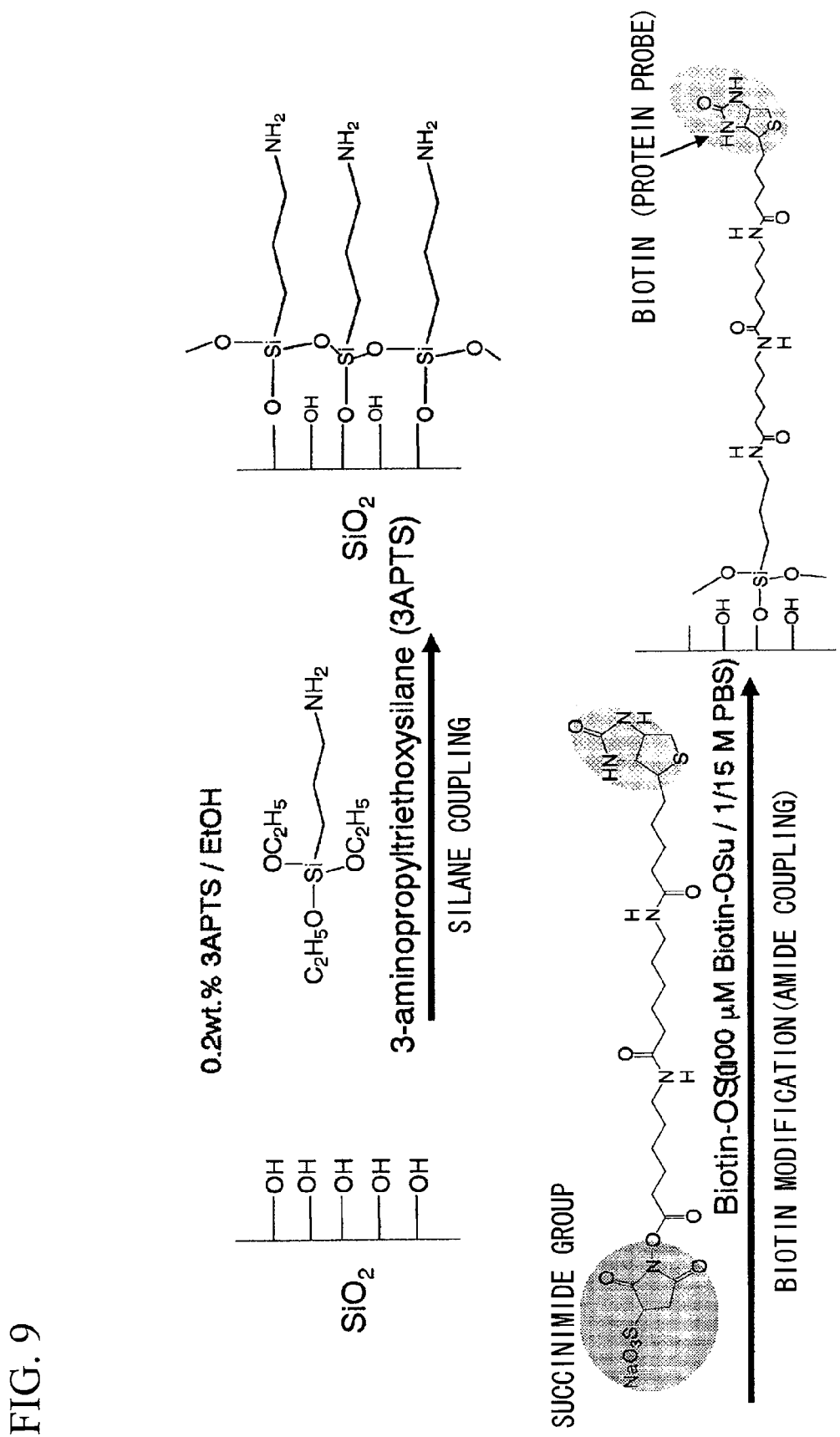
FIG. 9 shows diagrams explanatory of biotin chemical modification on a silicon oxide surface.
Figure 10:
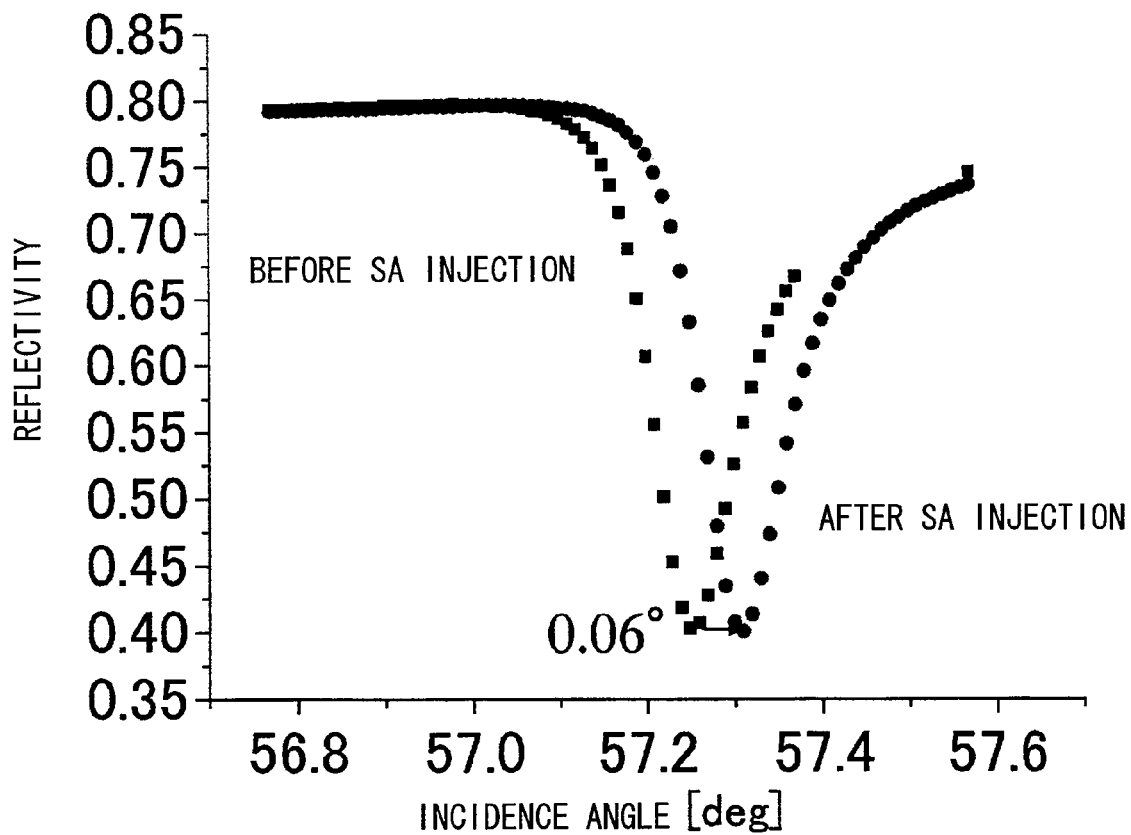
FIG. 10 is a graph showing the reflected light intensity characteristic measured by using specimen A in the Examples.
Figure 11:
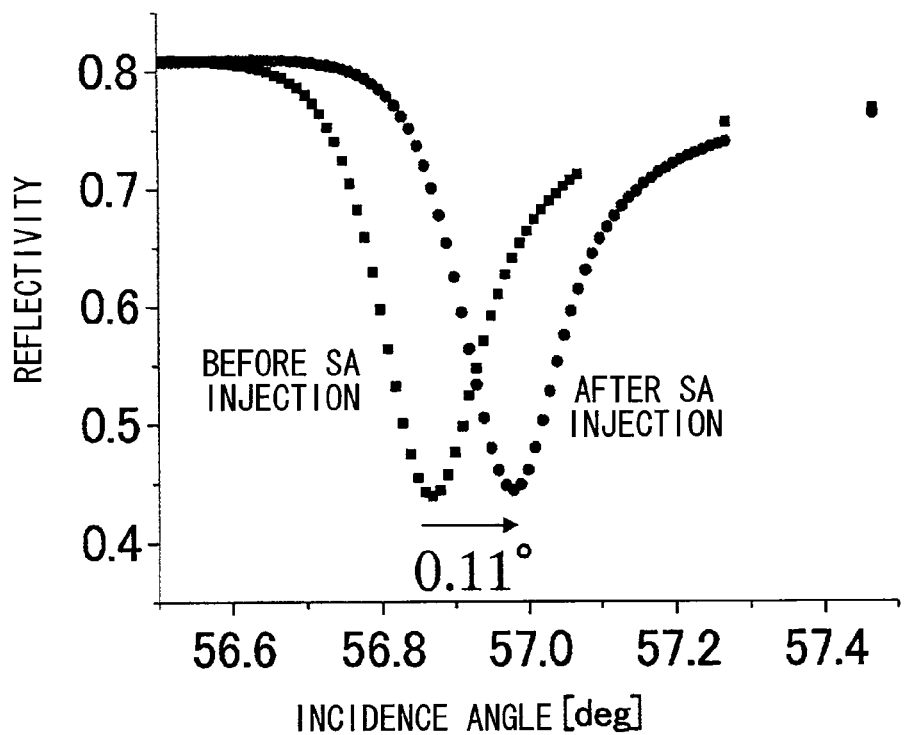
FIG. 11 is a graph showing the reflected light intensity characteristic measured by using specimen B in the present Examples.
Figure 12:
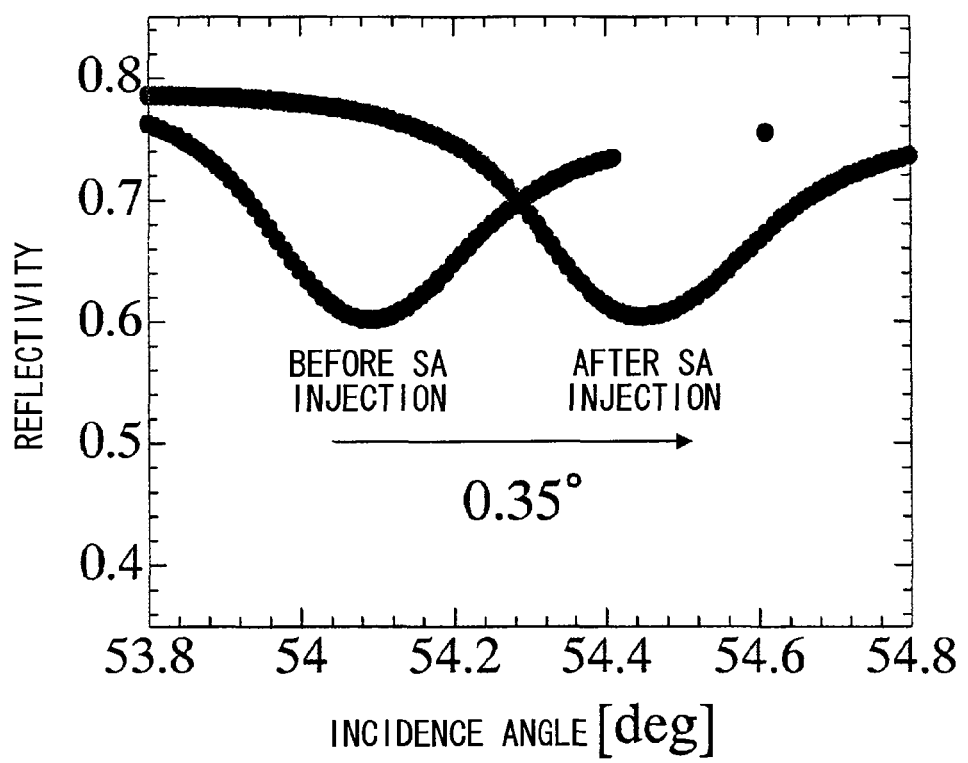
FIG. 12 is a graph showing the reflected light intensity characteristic measured by using specimen C in the present Examples.
Figure 13:
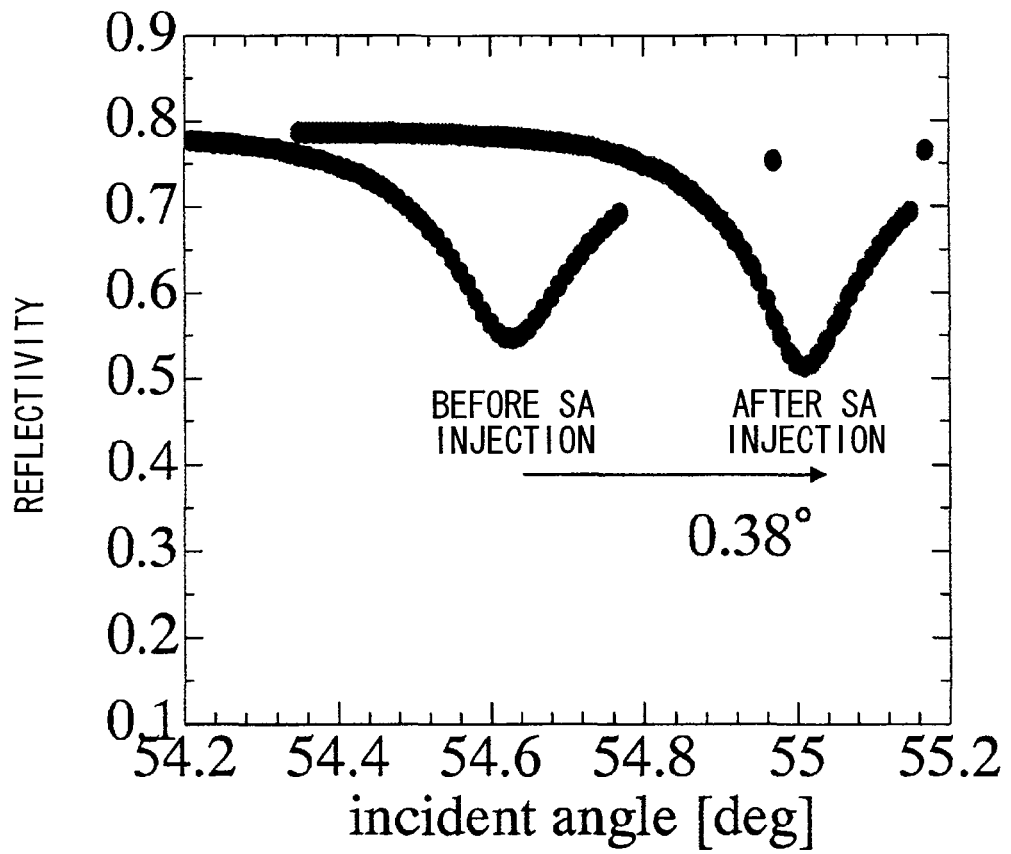
FIG. 13 is a graph showing the reflected light intensity characteristic measured by using specimen D in the present Examples.
Figure 14:
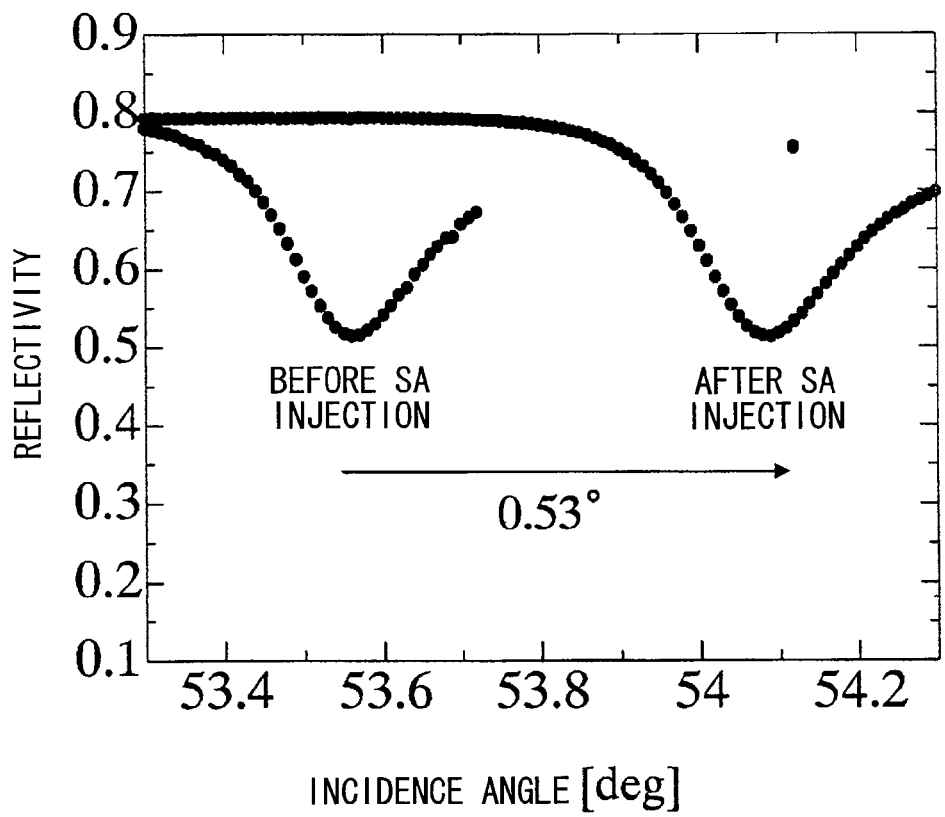
FIG. 14 is a graph showing the reflected light intensity characteristic measured by using specimen E in the present Examples.

All chips thus made were immersed in an aqueous weak alkali solution for one hour and were dried, and then immersed in an ethanol solution of 0.2 wt % 3-aminopropyltriethoxysilane for 2 hours thereby modifying a reactive amino group on the surface of a silicon oxide. After rinsing with ethanol and drying, the chips were immersed in 1/15 M phosphate buffer containing 0.1 mM sulfosuccinimidyl-N-(D-biotinyl)-6-aminohexanate. After standing for one hour, an amino group and a succinimide group were reacted thereby introducing a biothinyl group. FIG. 9 shows diagrams explanatory of biotin chemical modification on the silicon oxide surface. A hydroxyl group (—OH) protrudes on the surface of the silicon oxide (indicated as $SiO_2$ in the drawing) as the optical waveguide and an amino group (—$NH_2$) as an active group can be easily modified on the surface of a silicon oxide by immersing in a silane coupling agent such as 3-aminopropyltriethoxysilane. Furthermore, by immersing a substrate modified with an amino group in a solution prepared by dissolving a biotin compound having a succinimide group in a phosphate buffer (pH 7.4), biotin capable of specifically recognizing a protein (streptavidin) easily can be modified, and thus utility value as a biosensor is produced.

Then the chip was mounted on a liquid cell so that the optical waveguide surface makes contact with 1/15 M phosphate buffer. The surface opposite to the optical waveguide surface was put into contact with an optical prism via a refractive index matching oil. This assembly was mounted on a goniometer used in controlling the incident angle, and the substrate was irradiated with s-polarized light from a helium-neon laser (633 nm) via the optical prism.

For each of the chips, 1/15 M phosphate buffer containing 1 μM of streptoavidin (SA) that is adsorbed specifically onto a biotinyl group was poured into the liquid cell, and incidence angle dependency of the intensity of reflected light (reflectivity) was measured before and after pouring. Measurements with the specimens A, B, C, D and E are shown in FIGS. 10, 11, 12, 13 and 14, respectively. As can be seen from these figures, the incidence angle at which a sharp change in intensity of reflected light occurs is changed by the adsorption of streptoavidin. It can be seen that the amount of this change, namely, the amount of shift in the incidence angle at which the intensity of reflected light takes the minimum value, is increased by forming the pores.

Figure 15:
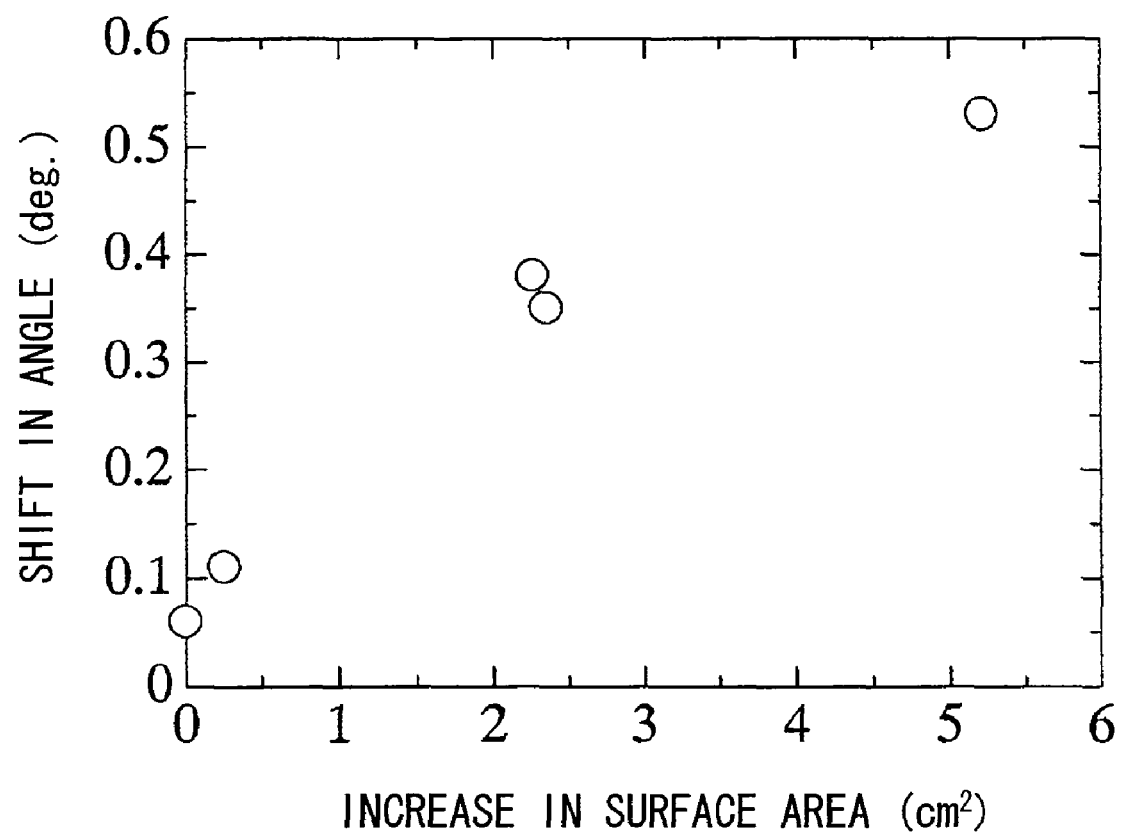
FIG. 15 is a graph of changes in the reflected light intensity characteristic plotted against the increase in surface area caused by forming pores in the present Examples.

Specimens B, C, D and E were cut off and observed under an electron microscope to measure the thickness of the optical waveguide layer, which was 530 nm, 430 nm, 450 nm and 440 nm, respectively. Differences between these values are supposedly caused by the difference in the etching conditions and the process error of sputtering. In every optical waveguide, the pores formed therein penetrated through the film and therefore had a depth equal to the thickness of the optical waveguide layer. Increase in the surface area per 1 cm$^2$ of the optical waveguide of the specimens B, C, D and E calculated using the depth, radius and number of the pores, was 0.25 cm$^2$, 2.35 cm$^2$, 2.26 cm$^2$ and 5.22 cm$^2$, respectively. FIG. 15 is a graph showing the relation between the increase in surface area and the amount of shift in the incidence angle at which the intensity of the reflected light becomes the minimum. It can be seen that higher sensitivity is obtained when the increase in surface area is greater. This graph also shows that the increase in surface area must be 0.1 cm$^2$ or greater in order to achieve an improvement in the sensitivity of a practically useful level.

INDUSTRIAL APPLICABILITY

The present invention, as described above, makes use of the optical waveguide mode of the optical waveguide having pores, and provides a remarkable effect of improving the sensitivity of detection, thus making it possible to detect a smaller specimen with a higher sensitivity without using labeling than in the case of the prior art technology that uses surface plasmon resonance and the optical waveguide mode. The optical waveguide mode sensor of the present invention is applicable in such fields as medicine, development of new drugs, foodstuff and environment, to be used as a biosensor that detects DNA, proteins, sugar chains or the like, and a chemical substance sensor that detects metal ions, organic molecules or the like. The optical waveguide mode sensor of the present invention is also applicable to a sensor for thin films and an instrument for measuring properties of thin film materials, as it is possible to measure the refractive index, relative dielectric constant and other properties of a thin film formed on the optical waveguide surface.

What is claimed is:

1. An optical waveguide mode sensor comprising:
a chip provided with a substrate formed from a transparent dielectric material or a transparent electrically-conductive material, a reflector film formed on the substrate, and an optical waveguide layer formed on the reflector film;
a plurality of pores formed in the optical waveguide layer so as to penetrate the optical waveguide layer;
a light-introducing mechanism that introduces light from the substrate side of the chip onto the reflector film; and
a light-detecting mechanism that detects the light reflected on the reflector film;
wherein a specimen under investigation is detected by sensing a change in an incidence angle or in an intensity of reflected light that occurs when the specimen is adsorbed or deposits on a surface of the optical waveguide layer, by using a range of incidence angles of the light in which the intensity of reflected light changes when a part or all of the incident light couples with the optical waveguide mode that propagates in the optical waveguide layer; and
wherein the optical waveguide is a film formed from a material selected from a group consisting of a silicon oxide, a titanium oxide, an organic material, a glass, a polymer, or a transparent electrically-conductive material, and
wherein the reflector film is a thin film of a semiconductor material.

2. The optical waveguide mode sensor according to claim 1, wherein the optical waveguide layer has a thickness in a range from 60 nm to 1 µm.

3. The optical waveguide mode sensor according to claim 1, wherein the pores are formed such that the total area of the inner wall surfaces of the pores, or the increase in surface area caused by forming the pores, is in a range not less than 0.1 cm$^2$ and not larger than 280 cm$^2$ per 1 cm$^2$ of the optical waveguide.

4. The optical waveguide mode sensor according to any one of claims 1, wherein a diameter of the pores is smaller than the wavelength of the light.

5. The optical waveguide mode sensor according to claim 1, wherein the pores are formed by chemical etching after implanting ions.

6. The optical waveguide mode sensor according to claim 5, wherein the chemical etching is an etching process by means of a hydrofluoric acid solution or a vapor of hydrofluoric acid.

7. The optical waveguide mode sensor according claim 1, wherein the optical waveguide layer has a thickness that causes the optical waveguide mode to develop.

8. The optical waveguide mode sensor according to claim 1, wherein a molecular recognition group is chemically modified on the surface of the optical waveguide layer.

9. The optical waveguide mode sensor according to claim 8, wherein any one of an amino group, a hydroxyl group, a carboxyl group, an aldehyde group, an isothiocyanate group, a succinimide group, a biotinyl group, a methyl group and a fluoromethyl group is chemically modified as the molecular recognition group.

10. The optical waveguide mode sensor according to claim 1, wherein the incident light is p-polarized or s-polarized light, and reflection of this light is detected.

11. The optical waveguide mode sensor according to claim 1, wherein the substrate has a plate configuration.

12. The optical waveguide mode sensor according to claim 1, wherein a surface of the substrate opposite to a side where the optical waveguide layer of the chip is formed is put into contact with an optical prism via a refractive index matching oil.

13. The optical waveguide mode sensor according to claim 1, wherein the substrate is a prism.

14. The optical waveguide mode sensor according to claim 12, wherein when p-polarized or s-polarized light enters the optical prism at an incidence angle with respect to a center axis of the prism, the incidence angle of the light is fixed proximate to the incidence angle at which the intensity of reflected light changes, and the intensity of reflected light is measured.

15. The optical waveguide mode sensor according to claim 8, wherein measurement is made on a film thickness, a weight, a size or a relative dielectric constant of a molecule, an ion or a cluster of molecules that is selectively adsorbed by or chemically bonds with a molecular recognition group that is chemically modified on the surface of the optical waveguide layer, in a gas or liquid.

16. An optical waveguide mode sensor chip used in the optical waveguide mode sensor according to claim 1.

17. The optical waveguide mode sensor according to claim 1, wherein the optical waveguide is a film formed from a silicon oxide.

* * * * *